United States Patent [19]

Nelson

[11] Patent Number: 4,923,680

[45] Date of Patent: May 8, 1990

[54] TEST DEVICE CONTAINING AN IMMUNOASSAY FILTER WITH A FLOW-DELAYING POLYMER

[75] Inventor: Roger W. Nelson, Fairport, N.Y.

[73] Assignee: Eastman Kodak Company, Rochester, N.Y.

[21] Appl. No.: 98,249

[22] Filed: Sep. 18, 1987

[51] Int. Cl.$^5$ .................. G01N 33/53; B01L 11/00
[52] U.S. Cl. .................... 422/58; 210/506; 422/61; 422/101; 435/7; 436/807
[58] Field of Search ............ 435/7; 436/518, 531, 436/807; 210/506–509; 422/101, 58, 61

[56] References Cited

U.S. PATENT DOCUMENTS

| 2,926,088 | 2/1960 | Spiselman | 210/506 |
| 3,272,742 | 9/1966 | Polishhuk | 210/506 |
| 3,888,629 | 6/1975 | Bagshawe | 436/542 X |
| 4,522,923 | 6/1985 | Deutsch | 436/810 X |
| 4,587,102 | 5/1986 | Nagatomo | 436/810 X |
| 4,615,983 | 10/1986 | Koyama | 436/531 X |
| 4,615,985 | 10/1986 | Deutsch | 436/531 |
| 4,618,533 | 10/1986 | Steuck | 428/315.7 |
| 4,632,901 | 12/1986 | Valkirs | 435/7 X |
| 4,681,782 | 7/1987 | Ozkan | 436/531 X |
| 4,727,019 | 2/1988 | Valkirs | 435/7 |

Primary Examiner—Robert J. Hill, Jr.
Attorney, Agent, or Firm—Dana M. Schmidt

[57] ABSTRACT

There is disclosed a filter and a device positioning the filter between an upper and a lower chamber, particularly useful in an immunoassay. The filter and device are improved in that the membrane comprising the filter is overcoated with at least one water-soluble polymer of a type, a molecular weight, and at a dry-solids coverage effective to create for that membrane an induction time at room temperature of at least about 30 seconds and no greater than about 300 seconds, for a liquid head of pressure of about 6 mm of water.

6 Claims, 1 Drawing Sheet

TEST DEVICE CONTAINING AN IMMUNOASSAY FILTER WITH A FLOW-DELAYING POLYMER

FIELD OF THE INVENTION

This invention relates to a filter and a test device using the same, effective to provide a delay time of flow therethrough of aqueous solutions. It is particularly applicable to a device for conducting an immunoassay on biological liquids.

BACKGROUND OF THE INVENTION

Disposable devices have been provided for conducting immunoassay tests for pregnancy and/or infectious diseases. Examples are described in U.S. Pat. No. 3,888,629. In such devices, there is a filter used to separate an upper reaction compartment from a lower compartment used to collect liquid that passes through the filter. Reagents comprising antigens or antibodies are often stored in the upper compartment, to react with an antibody or antigen, respectively, at the filter to produce a complex which is retained on the filter. The solvent passes through, carrying with it free, unreacted antigens and antibodies. Most preferably, the filter is sized to hold back just the complex that forms in the immunoassay of choice.

A problem has arisen in preparing such a device. Ideally, the reagents are applied to the upper chamber by coating them onto the top surface of the filter. However, the filter is designed to allow liquid to pass through containing such reagents in their uncomplexed form. Attempts to quickly dry the reagents have met with damage to the reagents if the drying temperature is too high. Thus, it has not been possible to apply the reagents as an overcoat, because the reagent solution passes through the filter before the solvent can be dried to leave the reagents on the top of the filter (or slightly penetrated into the top surface.) What has been desired is a filter that permits the reagents to be dried in place, and also permits eventual passing of liquid through the filter.

U.S. Pat. No. 4,587,102 teaches a test element comprising stacked layers of porous fabric, wherein the void volume is preferably 50 to 90%. A time-delay layer is added to the detection layer, col. 12. It comprises one or two water soluble polymers, which can be polyvinyl alcohol, polyvinyl pyrrolidone, or carboxymethyl cellulose. The amount is said to be from 2 to 50 microns in thickness, col. 13. These amounts in turn provide a dry coverage that is between about 2.2 g/m$^2$ to about 55 g/m$^2$. No suggestion is made that a particular induction time be achieved or that drying temperatures might create a problem.

SUMMARY OF THE INVENTION

I have constructed a time-delay filter for use in a disposable reaction device, between an upper and a lower compartment, having an induction time between about 30 and about 300 seconds, when measured at room temperature with a liquid head of pressure of about 6 mm.

More specifically, in accord with one aspect of the invention, there is provided a time-delay filter for filtering selected materials from an aqueous solvent in an immunoassay. The filter comprises a membrane having pores sized to retain the material on the filter, while passing through the solvent, and at least one water-soluble polymer on and within portions of the menbrane, the polymer being of a type, a molecular weight and a dry solids coverage effective to create for the membrane an induction time at room temperature of at least about 30 seconds and no greater than about 300 seconds, for a liquid head of pressure of about 6 mm of water.

In accord with a second aspect of the invention, there is provided a disposable reaction test device comprising an upper reaction compartment, a lower fluid collection compartment, and a filter separating the two compartments and comprising a membrane having pores sized to retain selected material and to pass through a solvent, the lower compartment including means for drawing liquid from the upper to the lower compartment through the filter. The device is improved in that the filter further comprises a water-soluble polymer on and within portions of the membrane, the polymer being of a type, a molecular weight and a dry solids coverage effective to create for the membrane an induction time at room temperature of at least about 30 seconds and no greater than about 300 seconds, for a liquid head of pressure of about 6 mm of water.

Accordingly, it is an advantageous feature of the invention that a time-delay filter and a reaction test device containing it, are provided wherein a reagent-containing overcoat can be applied and dried to the top of the filter, without losing the reagents through the filter.

It is a related advantageous feature of the invention that such a filter and device are provided that will allow customer-selected liquid to pass through the filter in a time not significantly exceeding about 5 minutes.

Other advantageous features will become apparent upon reference to the following detailed Description of the Preferred Embodiments, when read in light of the attached drawings.

DESCRIPTION OF THE PREFERRED EMBODIMENTS

Figure 1:
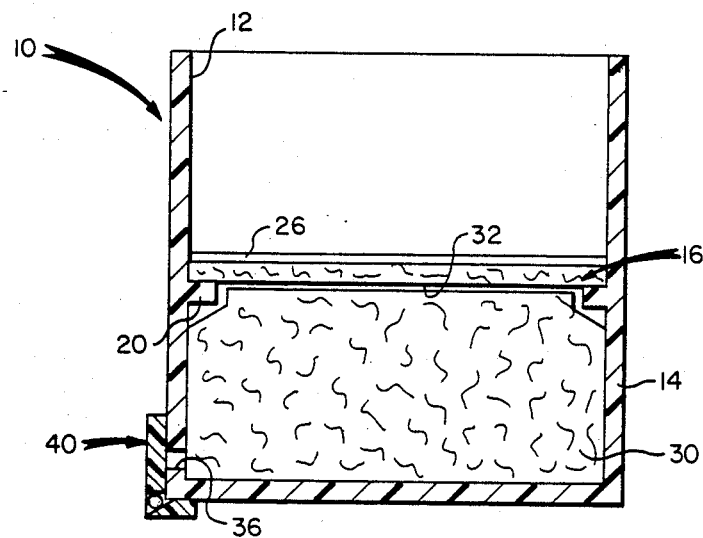
FIG. 1 is a vertical section view, partially schematic, of a device prepared in accordance of the invention.

The invention is described herein in connection with the preferred embodiments, that is, when used in a disposable reaction test device to filter out antibody-antigen complexes in an immunoassay, a reagent comprising an antibody or antigen having been preapplied to the top of the filter as an overcoat. In addition, the invention is useful to provide a time-delay filter in any device, to retain particles of any kind, wherein it is desired that the induction time at room temperature be at least about 30 seconds and no greater than about 300 seconds, for the stated liquid head of pressure.

As used herein, "induction time" refers to the amount of time it takes for the liquid applied to the top of the filter with a given head of pressure, to wet through to the bottom of the filter at room temperature. This delay in penetration of the filter is a function of the amount of, and properties of, the water-soluble polymer coated onto the membrane. The delay, of course, is caused by the re-dissolving of the polymer. The induction time must be long enough to allow reagents to be applied as an aqueous-based overcoat and dried without first passing through the filter, but short enough to allow a customer to use the device, that is, have the test liquid pass through in the appropriate length of time. The induction time allows the liquid to incubate in the presence of immunoreagents.

It has been found that the minimum induction time is partly a function of the temperature used to dry the overcoat of reagents. However, because most of such reagents are temperature sensitive, the maximum tolerable drying temperature is about 50° C. This in turn produces a drying time of about 30 seconds for the preferred wet coverages. Therefore, the induction time must be at least 30 seconds.

As to the maximum induction time, 5 minutes is the limit of tolerable waiting time for the customer. Most preferably, however, the induction time should not exceed about 200 seconds. The reasons for the preferred time of $\leq 200$ seconds are: (a) the customer's induction time arises from a second wetting of the device, the application of the overcoat being the first, and (b) the induction time for a second wetting is slightly longer than the induction time of the first wetting. Thus, the most preferred induction time of no greater than about 200 seconds allows for the fact that the customer's encountered induction time may be slightly longer.

Turning now to FIG. 1, a divice 10 prepared in accordance with the invention has an upper reaction compartment 12, a lower fluid-collecting compartment 14, and a filter membrane 16 disposed between the two compartments. Suitable means, such as a ledge 20, are used to hold membrane 16 in place. One or more water-soluble polymers are coated in one or more layers 26 on and into filter membrane 16. (Such layer(s) 26 may also penetrate into the membrane 16, even to the extent of not appearing as a separate layer above (not shown).)

An absorbent material 30 is provided in compartment 14, in fluid contact with bottom surface 32 of membrane 16. Any suitable absorbent material is useful. To vent compartment 14 to the atmosphere to avoid a liquid lock, an aperture 36 is provided. A suitable cover, such as hinged cover 40, is provided over aperture 36. Alternatively, a sliding cover (not shown) can be used. If only a single incubation of liquid above membrane 16 is required, cover 40 can be omitted since the overcoat layer 26 will appropriately delay flow. However, if plural incubation steps are required, cover 40 is included.

In actual use, it has been found desirable to have three such devices as shown in FIG. 1, joined together so that one can be used to test the patient's sample, one to test a positive control, and one to test a negative control. If an induction time is needed for all three, then the filter for each of the three is treated preferably as described herein.

With three such devices joined together, the filters act as follows. In one compartment, the patient's sample antigens, if any, complex with antibodies added by the user, some of which are labeled, so that the complex is unable to pass through the filter. If no antigen is present, all the labeled antibodies pass through after the induction time is exceeded, and are not available for detection. In a second compartment, antigen is supplied in the device as manufactured, and when antibody is added by the user, a complex forms as a positive control, and remains on the filter for detection. In a third compartment, no complexing will occur, unless the test conditions are improper, such as due to the presence of high amounts of salt, in which case the anti-complexing effect of a special anticomplexing agent that is present in the compartment, such as N-acetylglucosamine, is overcome and complexing occurs. Absence of signal in this compartment serves as a negative control.

The Membrane

Membrane 16 can be any thin microporous biologically inert material. As described in commonly owned U.S. application Ser. No. 098,433 filed on Sept. 18, 1987 by B. A. Snyder et al, entitled "Membrane Structure Coated with Low pI Protein or Carbohydrate and Methods of Making and Use", preferred materials are those that do not interact with the immunoreactive species of interest or its receptor, and include materials, such as glass, ceramics, fibers, synthetic and natural polymers and others known in the art. Thus, most preferred materials are cellulose esters, polyamides and polyesters. The polyamides, such as nylons, are most preferred.

The membrane structure has porosity and pore sizes sufficient for the intended use, whether it be filtration, assays or other likely uses. In the preferred embodiment of using the membrane structure in an agglutination immunoassay, the porosity is sufficient to allow fluids and unagglutinated materials to pass through but to not allow passage of agglutinated materials. In other words, the membrane pores, after coating, must be large enough to allow passage of any reagents and unagglutinated or uncomplexed particles, but not large enough to allow agglutinated or complexed paticles to pass through. For use in an agglutination assay, the average membrane pore size is at least about 5 times, and preferably from about 6 to about 15 times the average diameter of the agglutination reagent used therein. Most particularly, the average pore size of the membrane is generally less than about 10 micrometers, and preferably with 90% of the pore being less than about 5 micrometers in average transverse dimension. (As used herein, the size of the pores is measured as a dimension that is transverse to the long dimension of the pore, If the pore were cylindrical in shape, the transverse dimension would be a diameter.)

Useful membranes are commercially available from many sources. For example, useful polyamide materials include those available from Pall Biomedical Products Corp. (Glen Cove, N.Y.). A useful membrane is a nylon-66 microporous membrane manufactured and marketed by that company as BIODYNE A or ULTIPOR N-66. Useful cellulose acetate membranes are also commercially available. Useful membranes can be shaped to any desired configuration for a particular use.

The microporous membrane most preferably is precoated prior to its treatment described hereinafter, with one or more water-soluble proteins or carbohydrates. Generally, only one protein or carbohydrate is coated thereon, and is selected so that the protein and/or carbohydrate does not have a pI greater than 5.0.

The term pI is known as the pH at which there is an equal number of positive and negative charges so that the molecule is neutral in charge.

Useful water-soluble proteins include casein derivatives (for example, derivations obtained from acylation, alkylation or sulfonylation of casein), such as succinylated casein, succinylated bovine serum albumin, and succinylated collagen and other highly negative proteins or carbohydrates readily apparent to one skilled in the art. These materials are readily prepared by acylating, alkylating or sulfonylating a protein having available amine groups under suitable conditions to change the amine groups into carboxy, alkylcarboxy or sulfonyl groups, respectively. Useful acylating agents include, but are not limited to, those described in U.S. Pat. No. 4,591,571 (issued May 27, 1986 to Kuboyama et al), such as dicarboxylic anhydrides, polycarboxylic anhydrides, halides thereof and esters thereof. Succinic anhydride is a highly preferred acylating agent.

Alkylating and sulfonylating agents useful in modifying the proteins or carbohydrates described above include, but are not limited to bromoacetic acid, chloroacetic acid, fluoronitrobenzene, bromomalonic acid, bromopropionic acid, m-(chlorosulfonyl)benzoic acid and p-(chlorosulfonyl)benzoic acid. Bromoacetic acid is most preferred.

Useful carbohydrates include water-soluble cellulose derivatives. Representative compounds are carboxymethyl cellulose, carboxyethyl cellulose, and others which would be readily apparent to one skilled in the art. These materials are commercially available or can be readily prepared using known synthetic techniques.

Preferred pre-coating materials include succinylated casein, carboxymethyl cellulose, succinylated bovine serum albumin and succinylated collagen. Succinylated casein is most preferred.

The membrane structure can be prepared by contacting a microporous membrane of desired configuration with an aqueous solution of the appropriate proteins or carbohydrates by allowing a solution of the protein or carbohydrate to flow through the membrane at room temperature. In some cases, heating the solution up to 40° C. for several minutes prior to contact may be useful. The total protein or carbohydrate present in the solution is an amount sufficient to provide a coating over the entire membrane without substantially diminishing the porosity of the membrane. In other words, the pre-coating should completely cover the surface of the membrane, but be thin enough so that the pores of the membrane are not blocked to an undesirable extent. That is, at least 50% of the original porosity of the membrane prior to coating should be retained after the pre-coating. The amount of protein or carbohydrate needed to achieve these results can be varied depending upon the membrane porosity, solution viscosity and average pore size, but it is generally at least about 25 mg/cm$^2$. Very little of the protein or carbohydrate is left in the coating solution after membrane pre-coating.

The Water-Soluble Overcoat

Layer(s) 26 comprise at least one water-soluble polymer selected to have the appropriate molecular weight and solids coverage. I have found that the most preferred examples of such polymers are selected from the group consisting of polyvinyl alcohol, polyvinyl pyrrolidone, copolymers of either polyvinyl alcohol or polyvinyl pyrrolidone, carboxymethyl cellulose, carboxyethyl cellulose, poly(ethylene oxide), poly(acrylic acid), polyacrylamide, and poly(ethylene glycol). Useful examples of copolymers include a 50:50 or 90:10 (by mole ratio) copolymer of acrylamide and N-vinyl-2-pyrrolidone, and similar copolymers of acrylamide and acrylic acid. (As used herein, "polyvinyl alcohol" means, at least 75% hydrolized. The actual degree of hydrolysis is believed to be not critical.)

Regarding molecular weight, any weight is useful, provided the water-soluble polymer is adjusted as to its dry solids coverage. That is, I have found that polyvinyl alcohol will work at 2000 Daltons. A material that is much less than that in weight no longer qualifies as a polymer. Useful examples of Mw (weight-average molecular weight) have been found that extend up to about 360,000 Daltons. The layer(s) 26 are applied in one or more coatings that are dried between coatings.

Of critical importance is that the polymer(s) and the solids content selected provide the induction time that falls within the aforestated range. As noted, the minimum time is needed to allow a subsequent overcoat of reagents (not shown in the drawing) to be applied and dried prior to passing through membrane 16. Maximum temperatures for drying immunological reagents have been found to be about 50° C. At such a drying temperature for the subsequent overcoat, the induction time of layer(s) 26 need only be at least 30 seconds. However, if the drying temperature is reduced to 40° C., then the induction time needs to be at least 60 seconds, and so forth.

The amount of useful solids coverage of the polymer, varies depending upon the polymer selected, and upon the pore size and void volume of the membrane, as will be readily apparent. The following examples indicate useful amounts. Comparative examples are also included to indicate that merely selecting any coverage between 2.2 g/m$^2$ and 55 g/m$^2$ is no guarantee that layer(s) 26 will be provided that have the proper induction time. Instead, the proper selection of coverage for a given material and a given molecular weight is necessary, as is evident from the following test and examples.

Test

To ascertain whether a given polymer is useful at a given solids coverage, the following test is conducted:

A membrane as described above, with or without pretreatment with succinylated casein, is coated with the candidate polymer. The coated membrane is clamped in a three-well holder to a Webril cotton absorbant (of any thickness). 500 μl of a 0.01% Resazarin dye solution in either a 0.05M phosphate buffer at a pH of 7.0 or 0.1M glycine buffer at pH=8.6 that also contains 0.1M NaCl is placed in the center well so as to have a liquid head of pressure of about 6 mm. The induction time is the length of time required to initiate flow into the absorbent underneath, as is evident form the dye color.

EXAMPLES

The following examples further illustrate the scope of the invention. In these examples, the "Nylon disks" were 47 mm discs of Nylon obtained from the Pall Biomedical Corp. under the tradename Ultipor N-66, with either 3.0 or 5.0 μ nominal pore sizes. The "roll" of Nylon was a 5 μ nominal pore size roll obtained from the Pall Corp. under the tradename Ultipor N-66, in about 30 cm widths, slit to form widths of 12.5 cm. In all cases, the membranes had a void volume of from about 75 to about 85% with 90% of the pore sizes being less than or equal to 5 μ. Each of these was NOT precoated with succinylated casein, the reason being that such a precoat has no significant effect on the membrane porosity, as noted above. For simplicity, therefore, the precoating step was omitted. The tests were conducted by coating the membrane with a candidate water-soluble polymer as described, and then clamping the membrane with the holder noted in the test above, to the absorbant noted. The dye solution was applied as set forth in the "test".

EXAMPLES 1-3

Machine coatings of the polymers listed in Table I were applied to the roll material at a rate of about 300 cm/min. The coatings were dried at 40° C. and tested for induction time as described above, using the phosphate buffer solution. The results are presented in Table II.

TABLE I

| | Polymer Tested | | | |
|---|---|---|---|---|
| Ex. | Polymer | Mw (Daltons)* | Weight % of Solution | Dry Solids Coverage (g/m²) |
| 1 | polyvinyl alcohol obtained under TM "Vinol-205" from Air Products. | 11000 to 31000 | 20.6 | 41.2 |
| 2 | polyvinyl alcohol under TM "Vinol-523" from Air Products. | 77000 to 79000 | 11.7 | 19.5 |
| 3 | Carboxymethyl cellulose obtained under the TM "CMC-7M" from Hercules. | ~250,000 | 3.03 | 4.34 |
| Comp. Ex. 1 | polyvinyl pyrrolidone obtained under the tradename K-90 from GAF. | 360000 | 12.8 | 17.1 |
| Comp. Ex. 2 | Carboxymethyl cellulose obtained under the TM "CMC-7M" from Hercules. | ~250,000 | 3.03 | 6.52 |

*As provided by manufacturer.

TABLE II

| | Induction Times |
|---|---|
| Ex. | Induction Time (seconds) |
| 1 | about 50 |
| 2 | 66 |
| 3 | 40-65 |
| Comp. Ex. 1 | 6 |
| Comp. Ex. 2 | >600 |

It is useful to compare Ex. 2 with Comp. Ex. 1, and Ex. 3 with Comp. Ex. 2. In the first-named pair, dry solids coverages were comparable (19.5 versus 17.1); however, Comp. Ex. 1 gives an induction time that was much too fast, presumably due to the different polymer that was used. Even within the same polymer, a slightly different dry solids coverage can make a big difference, as noted in the comparison between Ex. 3 and Comp. Ex. 2—a 50% increase in dry solids coverage gave a 10-fold increase in induction time.

EX. 4-5 (PLURAL COATINGS)

In these examples, more than one coating of a water-soluble polymer was applied. The membranes were taken from the Nylon roll, and drying between coatings was done at the temperature noted in Table III. Dye was applied using the glycine buffer solution.

The results appear in Table IV. "Total flow time" is the time it took for the entire sample to flow through the filter. The difference between induction time and total flow time is the time it took for flow-through to occur once the absorbent underneath had been wetted.

TABLE III

| | Polymers Tested | | | |
|---|---|---|---|---|
| Ex. | Polymer | Mw (Daltons) | Weight % of Solution | Dry Solids Coverage (g/m²) | Drying Temp. |
| 4 | 1st - Carboxymethyl cellulose obtained under the TM "CMC-7M" from Hercules. | ~250,000 | 2.41 | 3.86 | 50° C. |
| | 2nd - polyvinyl pyrrolidone obtained from Eastman Kodak | 40,000 | 28.1 | 37.5 | 50° C. |
| 5 | 1st - Carboxymethyl cellulose obtained under the TM "CMC-7M" from Hercules. | ~250,000 | 2.41 | 3.86 | 50° C. |
| | 2nd - polyvinyl pyrrolidone (K-90) | 360,000 | 12.6 | 15.5 | 32° C. |
| Comp. Ex. 3 | 1st - Carboxymethyl cellulose obtained under the TM "CMC-7M" from Hercules. | ~250,000 | 2.41 | 3.4** | 50° C. |
| | 2nd - polyvinyl pyrrolidone (K-90) | 360,000 | 12.6 | 15.5 | 32° C. |
| | 3rd - polyvinyl pyrrolidone (K-90) | 360,000 | 19.6 | 7-9 | 32° C. |
| Comp. Ex. 4 | 1st - Carboxymethyl cellulose obtained under the TM "CMC-7M" from Hercules. | ~250,000 | 2.41 | 3.86 | 50° C. |
| | 2nd - polyvinyl pyrrolidone (K-90) | 360,000 | 12.6 | 15.5 | 32° C. |
| | 3rd - polyvinyl alcohol obtained under TM "Vinol-205" from Air Products. | 11,000 to 31,000 | 19.6 | 7-9 | 32° C. |

**This is less than, e.g., Ex. 5, because the wet coat lay-down was less in thickness.

TABLE IV

| | Induction Times | |
|---|---|---|
| Ex. | Induction Times (seconds***) | Total Flow Time (sec) |
| 4 | 30-45 | 70-85 |
| 5 | 55-65 | 130-155 |
| Comp. Ex. 3 | 575-700 | (635-800) |
| Comp. Ex. 4 | 610-700 | (675-785) |

***A range appears here because of repeated tests of 6-8 samples that gave an extended range.

A comparison between Ex. 5 and Comp. Ex. 3 is instructive. The latter is identical to the former, except that it includes the extra 7-9 g/m² coverage of polyvinyl pyrrolidone (dry solids coverage). That is enough to push the induction time well beyond the maximum time of 300 seconds.

EX. 6-7 (ADDITIONAL PLURAL COATINGS PLUS GLYCEROL)

In these examples, the materials used were varied slightly from those of Ex. 4 and 5, and in addition, small amounts of glycerol were added to minimize curl. Coatings were again achieved via machine coating, on the roll form of Nylon without succinylated casein.

TABLE V

| Ex. | Polymer | Mw (Daltons*) | Weight % of Polymer in Solution | Dry Solids | Drying Temp. |
|---|---|---|---|---|---|
| 6 | 1st - polyvinyl pyrrolidone (K-30) obtained from GAF plus 4.2 wt. % glycerol. | 40,000 | 41.6 | 55.2 g/m² | 26.5° C. |
|   | 2nd - polyvinyl pyrrolidone (K-90) plus 1.35 wt. % glycerol. | 360,000 | 12.8 | 13.7 g/m² | 26.5° C. |
| 7 | 1st - mixture of K-90 and K-30 of Ex. 6, plus 2.8 wt. % glycerol | 40,000 360,000 | 7.1% K-90, 20.6% K-30 | 36.7 g/m² | 26.5° C. |
|   | 2nd - K-90 of Ex. 6 plus 1.35 wt. % glycerol. | 360,000 | 12.8 | 13.7 g/m² | 26.5° C. |

The results appear in Table VI:

TABLE VI

| | Induction Times | |
|---|---|---|
| Ex. | Induction Times | Total Flow Time |
| 6 | 145 seconds | 162 seconds |
| 7 | 175 seconds | 190 seconds |

A comparison between Ex. 4–5, and Ex. 6–7 indicates that Ex. 6–7 are preferred. The reason is that, once wet-through occurs, the flow is more rapid (15 to 20 seconds) in those examples, than in Ex. 4–5, in which it took about 40 seconds (Ex. 4) or 80 seconds (Ex. 5) for the liquid to flow through.

The invention has been described in detail with particular reference to preferred embodiments thereof, but it will be understood that variations and modifications can be effected within the spirit and scope of the invention.

What is claimed is:

1. In a reaction test device, comprising an upper reaction compartment, a lower fluid collection compartment, and a filter separating the two compartments and comprising a membrane having pores sized to retain selected material and to pass through a solvent, said lower compartment including means for drawing liquid from the upper to the lower compartment through the filter, the improvement wherein said filter further comprises a first water-soluble polymer on and within portions of said membrane, and an additional water-soluble polymer applied on said at least one polymer after the latter is dry, said polymers being of a type, a molecular weight and a dry solids coverage effective to create for said membrane an induction time at room temperature of at least about 30 seconds and no greater than about 300 seconds, for a liquid head of pressure of about 6 mm of water.

2. A device as defined in claim 1, wherein said first polymer is selected from the group consisting of polyvinyl alcohol, polyvinyl pyrrolidone and copolymers thereof, carboxymethylcellulose, and carboxyethylcellulose.

3. A device as defined in claim 1 wherein said additional polymer is selected from the group consisting of polyvinyl alcohol, polyvinyl pyrrolidone and copolymers thereof, carboxymethylcellulose, and carboxyethylcellulose.

4. A device as defined in claim 1 wherein said additional polymer and said at least one polymer have the same chemical structure but different molecular weights.

5. A device as defined in claim 1, and further including an immunoreagent on said filter, selected from an antibody or an antigen.

6. A test device as defined in claim 1, wherein said second polymer is applied together with about 1 to 3 wt % glycerol.

* * * * *